United States Patent [19]
Klaus et al.

[11] Patent Number: 5,801,253
[45] Date of Patent: Sep. 1, 1998

US005801253A

[54] RETINOIC ACID X-RECEPTOR LIGANDS

[75] Inventors: Michael Klaus, Weil am Rhein, Germany; Allen John Lovey, North Caldwell, N.J.; Peter Mohr, Basel, Switzerland; Michael Rosenberger, North Caldwell, N.J.

[73] Assignee: Hoffmann-La Roche Inc., Nutley, N.J.

[21] Appl. No.: 776,087

[22] PCT Filed: Jul. 29, 1995

[86] PCT No.: PCT/EP95/03021

§ 371 Date: Jan. 21, 1997

§ 102(e) Date: Jan. 21, 1997

[87] PCT Pub. No.: WO96/05165

PCT Pub. Date: Feb. 22, 1996

[30] Foreign Application Priority Data

Aug. 10, 1994 [EP] European Pat. Off. ............... 94112461
Jul. 5, 1995 [EP] European Pat. Off. ............... 95110460

[51] Int. Cl.[6] ............... C07D 333/08; C07C 63/00; C07C 69/76; C07C 233/00
[52] U.S. Cl. ............... 549/79; 562/405; 562/490; 560/8; 560/100; 564/180; 556/465; 556/489

[58] Field of Search ............... 549/79; 562/405, 562/490; 560/8, 100; 564/180; 556/465, 489

[56] References Cited

U.S. PATENT DOCUMENTS

| | | | |
|---|---|---|---|
| 4,703,110 | 10/1987 | Shudo | 534/566 |
| 5,344,959 | 9/1994 | Chandraratna | 560/100 |
| 5,466,861 | 11/1995 | Dawson et al. | 560/100 |

OTHER PUBLICATIONS

Breitman et al., Proc. Nat. Acad. Sci. USA, 77:2936–2940 (1980).

J. Org. Chem., 46:5159–5163 (1981).

*Primary Examiner*—Deborah Lambkin
*Attorney, Agent, or Firm*—George W. Johnston; Dennis P. Tramaloni; Bruce A. Pokras

[57] ABSTRACT

Compounds of formula (I) wherein $R^1$–$R^7$, $R^{10}$, X and the dotted bond have the meaning given in the specification, bind selectively to retinoid RXR receptors and are useful as antiproliferative agents for dermatological and oncological indications.

22 Claims, 3 Drawing Sheets

RETINOIC ACID X-RECEPTOR LIGANDS

This application is a 371 of PCT/EP95/03021 Jul. 29, 1995.

The present invention relates to novel retinoic acid X-receptor (RXR) ligands. More particularly, the present invention relates to compounds of the formula I:

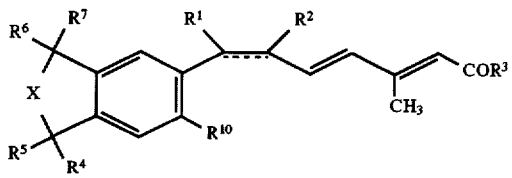

wherein the dotted bond is optional; and, when the dotted bond is present, $R^1$ is lower alkyl and $R^2$ is halogen, or $R^1$ and $R^2$ taken together with the carbon atoms to which they are attached form a 5–8 membered carbocyclic ring or a 5–8 membered heterocyclic ring containing one sulfur, oxygen or nitrogen atom, wherein, when said ring is aromatic, the dotted bond is part of the mesomeric system; or, when the dotted bond is absent, $R^1$ and $R^2$ taken together are methylene to form a cis-substituted cyclopropyl ring; $R^3$ is hydroxy or lower alkoxy; $R^4$, $R^5$, $R^6$ and $R^7$ are, independently, hydrogen or lower alkyl; X is $(>CR^8R^9)_n$; and n is 1,2 or 3; $R^8$, $R^9$ are, independently, hydrogen or lower alkyl; $R^{10}$ is hydrogen, alkyl or alkoxy;

and pharmaceutically acceptable salts of carboxylic acids of formula I.

As used herein the term "lower" denotes groups containing 1–4 carbon atoms. Lower alkyl groups may be straight chained or branched. Preferred are methyl and ethyl. The term "halogen" includes fluorine, chlorine, bromine and iodine with bromine being preferred. Examples of 5–8 membered carbocyclic rings formed by $R^1$ and $R^2$ together with the carbon atoms to which they are attached are benzene, cyclopentene, cyclohexene, cycloheptene of which benzene is preferred. Examples of 5–8 membered heterocyclic rings formed by $R^1$ and $R^2$ together with the carbon atoms to which they are attached are thiophene, furan, dihydro furan and pyridine of which thiophene is preferred. $R^4$–$R^7$ are preferably lower alkyl, most preferably methyl. X is preferably ethylene. $R^{10}$ is preferably hydrogen. When the optional dotted bond is present and part of the mesomeric system of an aromatic ring, this means that the additional bond is considered to be delocalized over the ring as described in the classical model of aromaticity.

The compounds of formula I wherein $R^3$ is hydroxy form salts with pharmaceutically acceptable bases such as alkali salts, e.g. Na and K-salts, and ammonium or substituted ammonium salts such trimethylammonium salts which are within the scope of this invention.

In one aspect the invention comprises compounds of the formula:

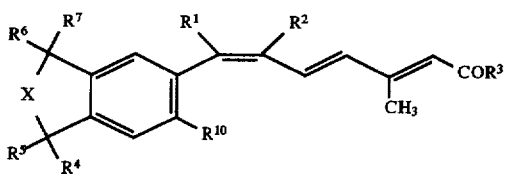

wherein $R^1$ is lower alkyl and $R^2$ is halogen, or $R^1$ and $R^2$ taken together with the carbon atoms to which they are attached form a 5–8 membered carbocyclic ring or a 5–8 membered heterocyclic ring containing one sulfur, oxygen or nitrogen atom, wherein, when said ring is aromatic, the double bond between the carbon atoms adjacent to $R^1$ and $R^2$ is part of the mesomeric system; $R^3$–$R^7$, $R^{10}$ and X are as in formula I;

and pharmaceutically acceptable salts of carboxylic acids of formula Ia.

In another aspect the invention preferably comprises compounds of the formula:

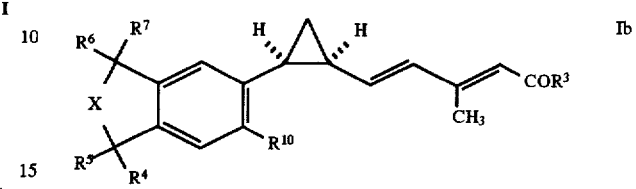

wherein $R^3$–$R^7$, $R^{10}$ and X are as in formula I;
and pharmaceutically acceptable salts of carboxylic acids of formula Ib.

Especially preferred compounds of formula Ia are compounds of the formula:

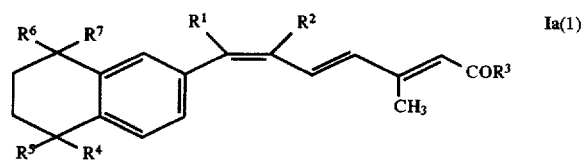

wherein $R_1$ through $R^7$ are as in formula Ia. Particularly preferred are compounds of formula Ia(1) in which $R^4$–$R^7$ are all methyl, and $R^1$–$R^3$ are as in formula Ia. Most preferred are compounds of formula Ia(1) in which $R^4$–$R^7$ are all methyl and $R^3$ is hydroxyl and $R^1$–$R^2$ are as in formula Ia.

Especially preferred compounds of formula Ib are compounds of the formula:

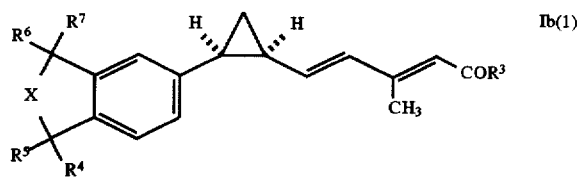

wherein $R^1$ through $R^7$ are as in formula Ib. Particularly preferred are compounds of formula Ib(1) in which $R^4$–$R^7$ are all methyl, and $R^3$ is as in formula Ib.

The invention also comprises the pharmaceutically acceptable salts of carboxylic acids of the compounds of formulas Ia(1) and Ib(1).

The compounds of this invention demonstrate a high degree of selectivity toward the RXR family of receptors. They are useful as anti proliferative agents and have utility for dermatological and oncological indications. In particular, the compounds of the invention inhibit proliferation of sebocytes, and so are useful for the treatment of acne.

WO-A-9504036 discloses RXR selective tetrahydronaphthalene derivatives that may contain an aliphatic trienoic acid side chain. GB-A-2 122 200 discloses tetrahydronaphthyl dimethyloctatrienoic acid derivatives that are suitable for the treatment of neoplasms and dermatoses.

The compounds of the invention also, at doses at which they are inactive by themselves, increase the activity of compounds which bind to retinoic acid receptors (RAR). An example of such an RAR-selective retinoids is all-trans retinoic acid. Thus, the administration of the compounds of the invention in combination with an RAR-selective retinoid allows the use of much lower doses of the RAR-selective retinoid for indications in which such RAR-selective retinoid is used. One such indication is the treatment of human leukemia.

The compounds of this invention can also be used in combination with ligands for other nuclear receptors of the same superfamily which form heterodimers with RXR, e.g., vitamin D compounds or thyroid hormones thereby increasing their effect.

HL-60 is a human myeloid leukemia cell line which is exquisitely sensitive to retinoid-induced differentiation (see Breitman et al., Proc.Nat.Acad.Sci.USA 1989, 86, 7129–7133) and can thus be used as a model for testing cell-differentiation inducing activity. The induction of HL-60 differentiation is a standard model for the treatment of human leukemia. The differentiation of HL-60 cells was assayed by measuring their oxidative potential via the reduction of nitrobluetetrazolium (NBT). HL-60 cells were maintained in RPMI 1640 medium supplemented with 105 FCS, 2 mM L-glutamine, 1 mM sodium pyruvate, 1% nonessential amino acids, 50 U/ml penicillin and 50 microgram/ml streptomycin. The cells were found to be free of mycoplasma. 30,000 cells/100 microliter of RPMI/FCS were seeded into flat-bottom microtiter wells. 10 microliter of a retinoid solution diluted in complete medium were added at the same time to yield final concentrations between $10^{-11}$ and $10^{-6}$M (stock solutions of $10^{-2}$M in ethanol were kept at −20° C. and protected from light). After 3 days the medium was removed with a multichannel pipette and replaced with 100 microliter of NBT solution (1 mg/ml in PBS with 200 nM phorbol myristate acetate). Following an additional hour incubation at 37° C. the NBT solution was removed and 100 microliter of 10% SDS in 0.01 N HCl was added. The amount of the reduced NBT was quantified photometrically at 540 nm using an automated plate reader. The mean of 3 wells was calculated. S.E.M. were between 5 and 10%.

BRIEF DESCRIPTION OF DRAWINGS

In FIGS. 1–6, Compound A is (2E,4E)-3-methyl-5-[3-(5,5,8,8-tetramethyl-5,6,7,8-tetrahydro-naphthalen-2-yl)-thiophen-2-yl]-penta-2,4-dienoic acid (Example 2);

Figure 1:
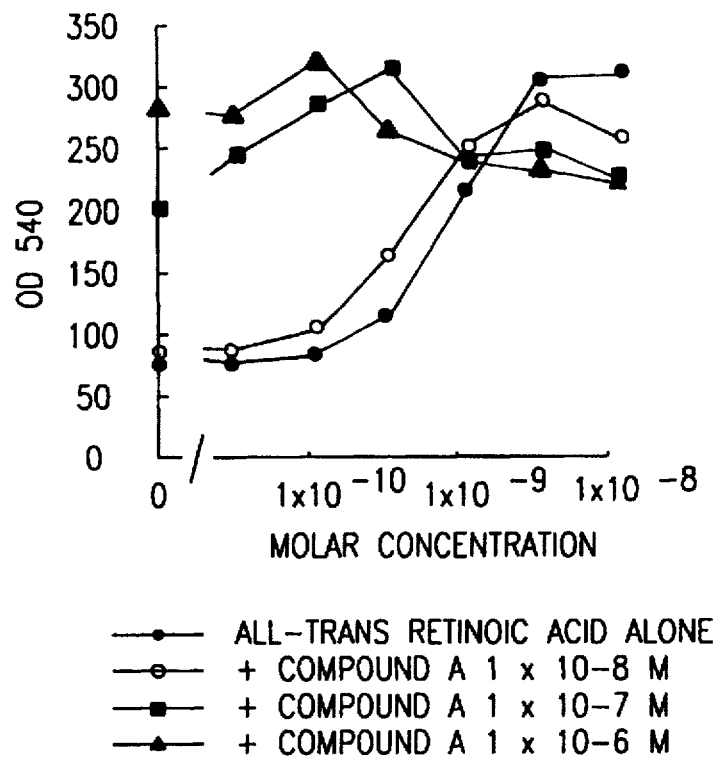
FIGS. 1–6 show the effect of all-trans retinoic acid alone and in combination with compounds of the present invention in inducing HL-60 cell differentiation.
Figure 2:
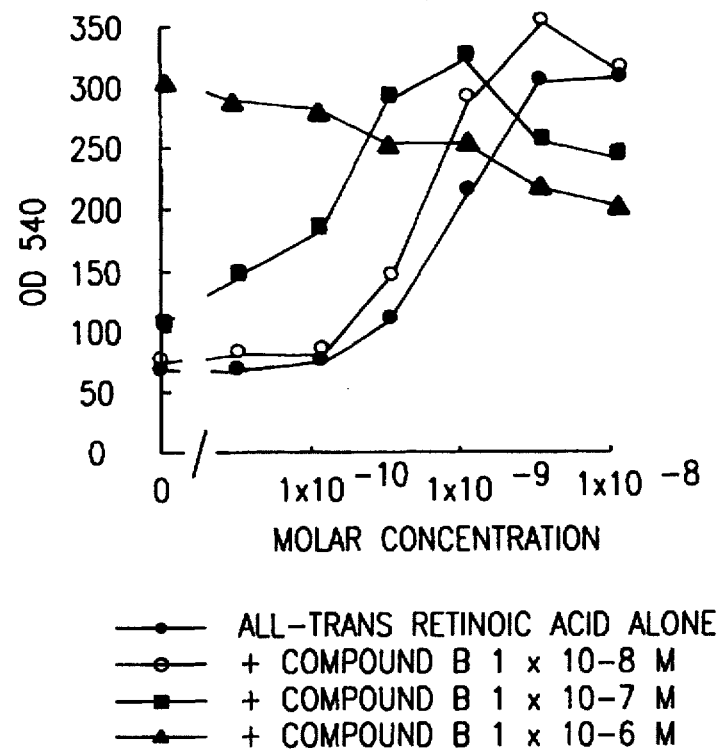
Figure 3:
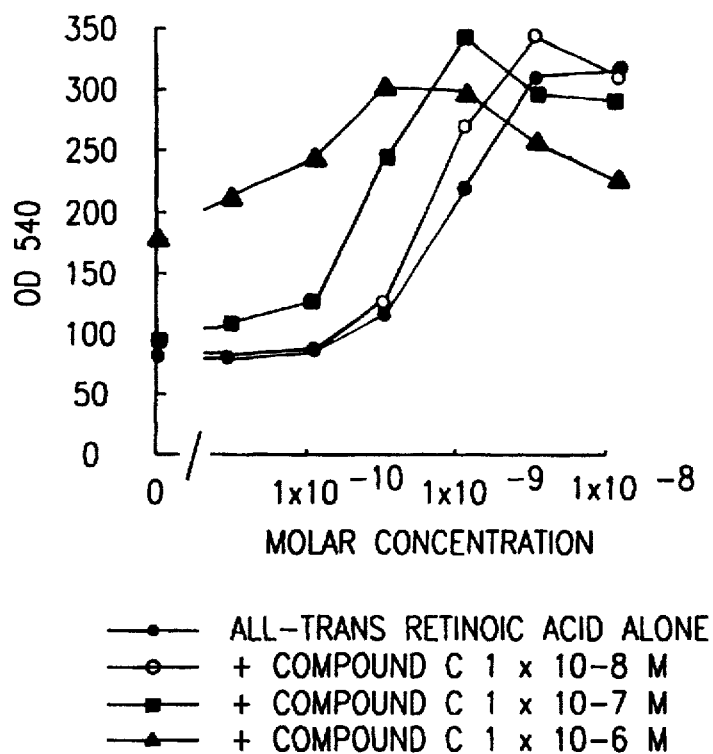
Figure 4:
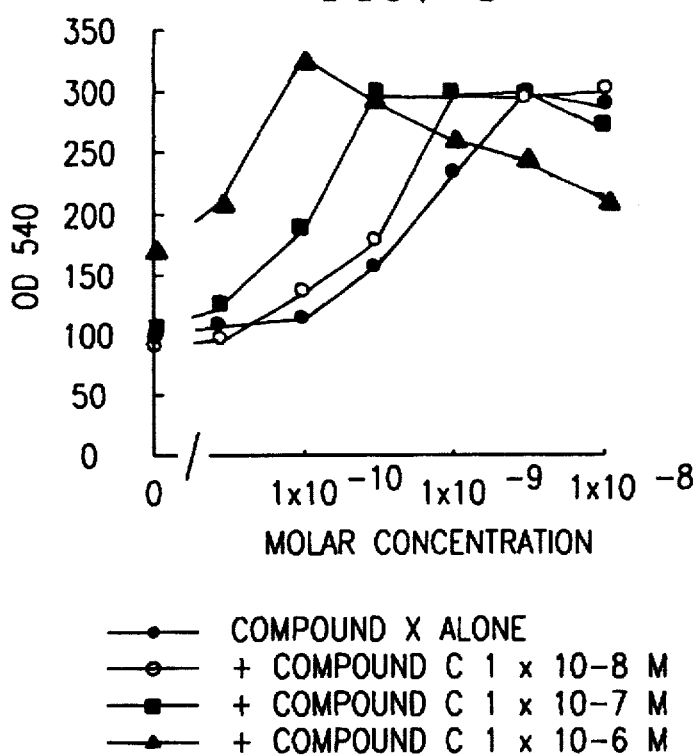
Figure 5:
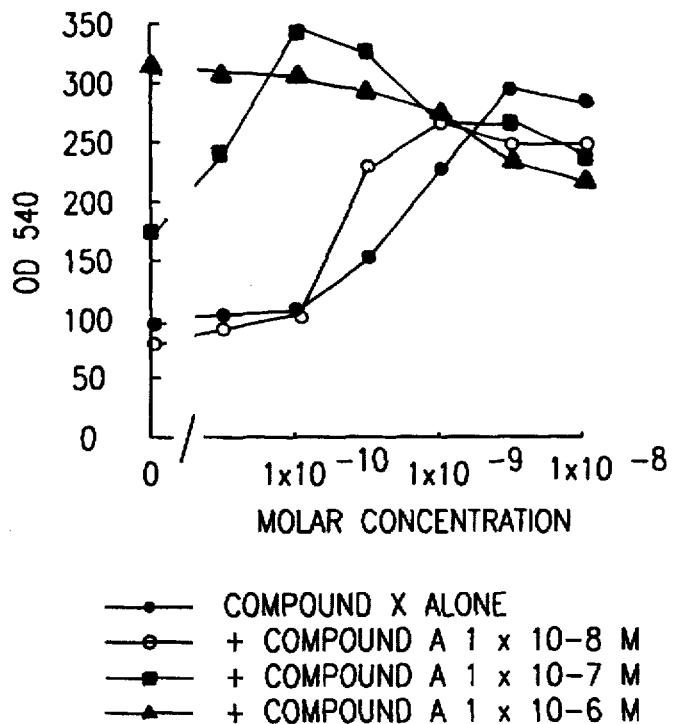
Figure 6:
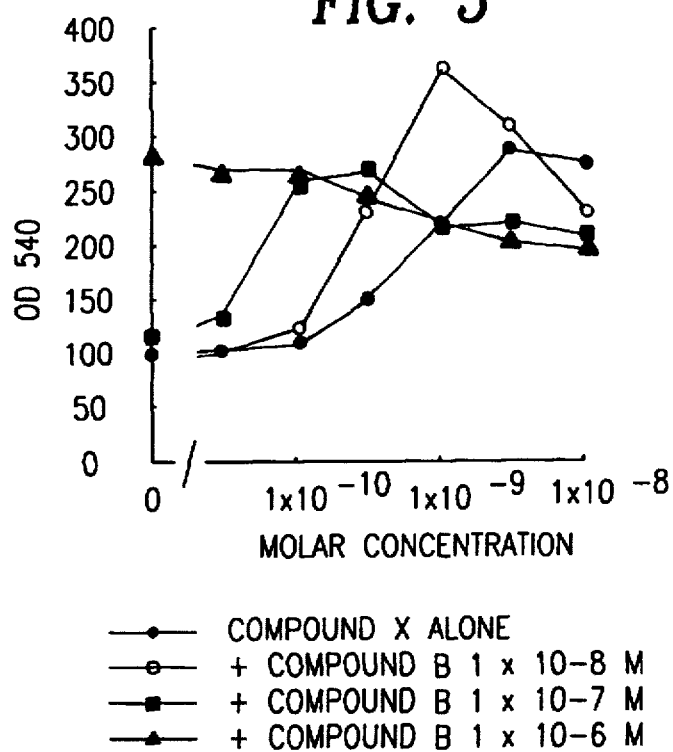

Compound B is (2E,4E)-3-methyl-5-[(1RS,2RS)-2-(5,5,8,8-tetramethyl-5,6,7,8-tetrahydro-naphthalen-2-yl)-cyclopropyl]-penta-2,4-dienoic acid (Example 6);

Compound C is (2E,4E)-3-methyl-5-[2-(5,5,8,8-tetramethyl-5,6,7,8-tetrahydro-naphthalen-2-yl)-phenyl]-penta-2,4-dienoic acid (Example 1);

Compound X is p-(5,5,8,8,-tetramethyl-5,6,7,8-tetrahydro-2-naphthalenecarboxamido)-benzoic acid (see, e.g. U.S. Pat. No. 4,703,110).

From the results obtained it is obvious that the effect of the compounds of this invention and all-trans retinoic acid is more than additive.

Accordingly, the compounds of this invention can find use in the treatment of conditions that are mediated by retinoid receptors. For example, the compounds of this invention may be used in the treatment and prevention of dermatological conditions such as acne or psoriasis. The compounds of this invention have reduced toxicity or teratogenicity as compared to classical RAR-selective retinoid compounds such as all-trans retinoic acid. The compounds of this invention may be administered together with RAR-selective retinoids thus reducing the dosage of such retinoids and the risk of unwanted effects connected to such treatment.

In accordance with the present invention the compounds of formula I can be prepared by reacting a compound of formula II

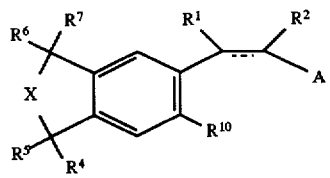

with a compound of formula III

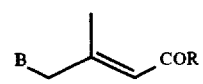

wherein A is formyl and B is triarylphosphonium or di-(lower alkoxy)phosphinyl; or A is triarylphosphonium or di-(lower alkoxy)phosphinyl and B is formyl; R is lower alkoxy; and $R^1$, $R^2$, $R^4$, $R^5$, $R^6$, $R^7$ and $R^{10}$ are as defined above;

to yield a compound of formula I wherein $R^3$ is lower alkoxy, and, if desired, hydrolysing the lower alkoxy group $R^3$ in the so obtained compound of formula I.

The reaction of the compound II with the compound III can be carried out according to methods which are known per se for the Wittig or Horner reaction.

The reaction wherein one of the compounds of formula II and III contains a triaryl (preferably triphenyl)phosphonium group (Wittig reaction) can be effected in the presence of an acid-binding agent, e.g. a strong base such as e.g. butyllithium, sodium hydride or the sodium salt of dimethyl sulphoxide, but primarily in the presence of an ethylene oxide which is optionally substituted by lower alkyl, such as epoxybutane, optionally in a solvent, e.g. in an ether such as diethyl ether or tetrahydrofuran or in an aromatic hydrocarbon such as benzene, in a temperature range lying between room temperature and the boiling point of the reaction mixture. The anion to the phosphonium group can be an inorganic anion such as chloride or bromide or hydrogen sulfate, or an organic anion such as tosylate.

The reaction wherein one of the compounds of formula II and III contains a dialkoxyphosphinyl group (Horner reaction) can be carried out in the presence of a base and, preferably, in the presence of an inert organic solvent, e.g. in the presence of sodium hydride in benzene, toluene, dimethylformamide, tetrahydrofuran, dioxane or a 1,2-dimethoxyalkane, or also a sodium alcoholate in an alkanol, e.g. sodium methylate in methanol, in a temperature range lying between 0° and the boiling point of the reaction mixture. In a preferred aspect of the invention, the compounds of formula I are prepared by reacting a compound of formula II wherein A is formyl with a compound of formula III wherein B is di-(lower alkoxy)phosphinyl.

A thus-obtained carboxylic acid ester of formula I can be hydrolyzed in a manner known per se, e.g. by treatment with alkalis, especially by treatment with aqueous-alcoholic sodium or potassium hydroxide solution in a temperature range lying between room temperature and the boiling point of the reaction mixture.

The thus-obtained carboxylic acid of formula I can be isolated in a manner known per se as such or as a salt, e.g. as an alkali salt, especially as the Na or K salt.

The compounds of formula II are novel compounds and are also an object of the present invention. The compounds of formula II can be prepared as set forth in Schemes 1,2 and 3 below wherein R is lower alkyl, Z is bromine or iodine, and $R^1$, $R^2$ and $R^4$–$R^7$ and $R^{10}$ are as defined earlier:

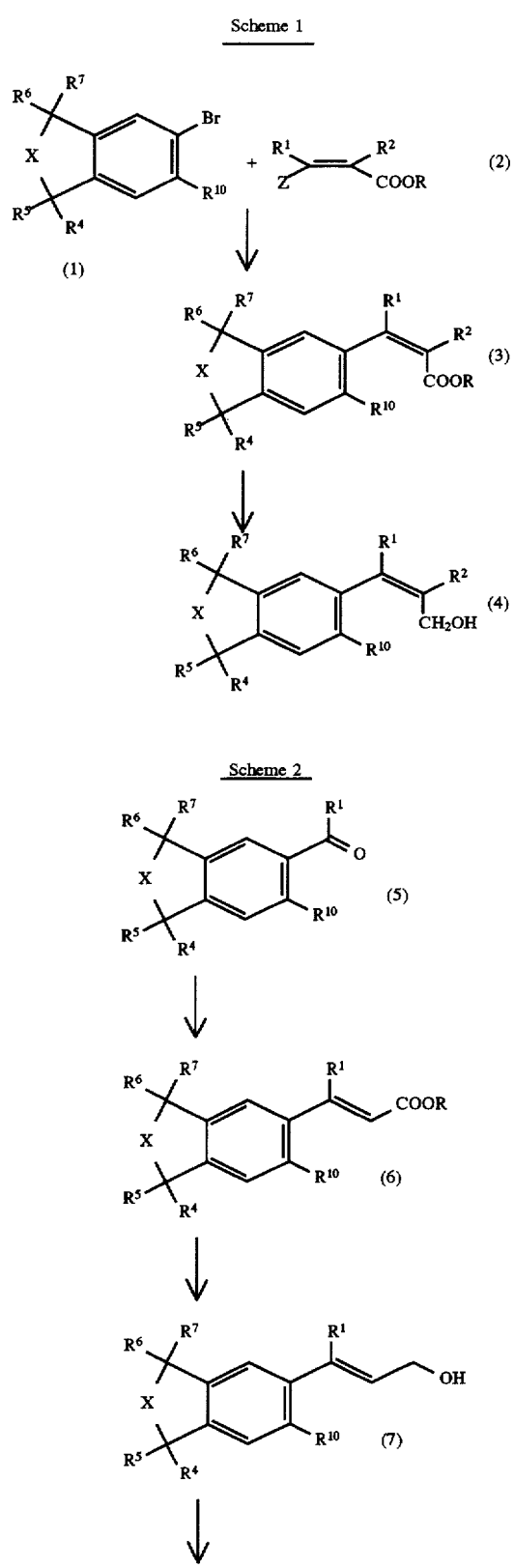

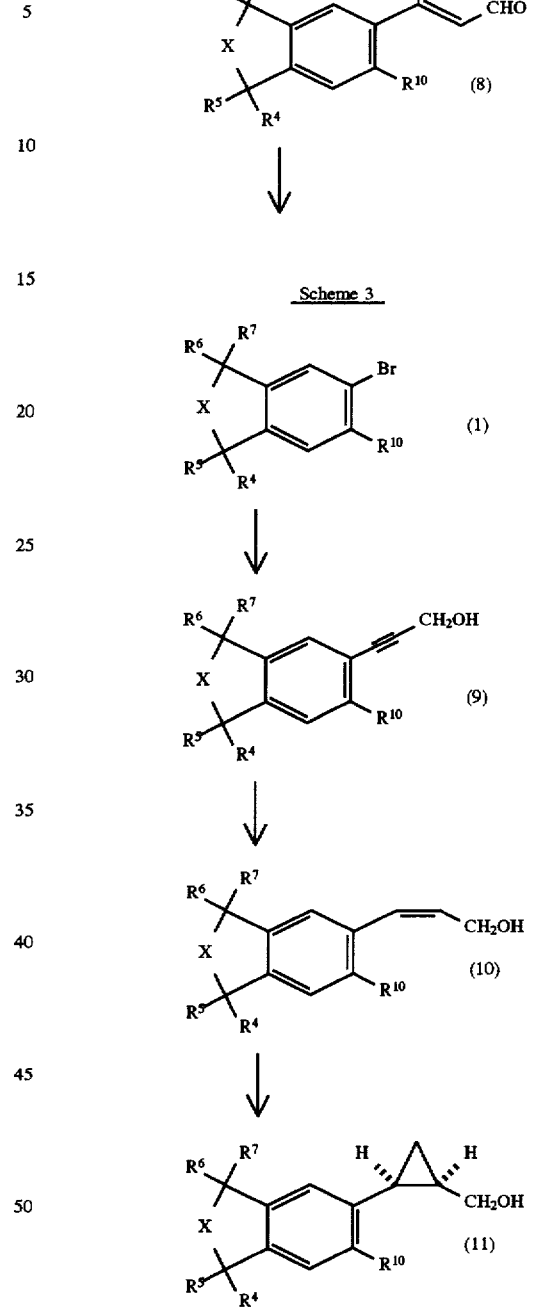

Compounds of formula II wherein the dotted bond is present, $R^1$ is lower alkyl and $R^2$ is hydrogen;or $R^1$ and $R^2$ taken together with the carbon atoms to which they are attached form a 5–8 membered aromatic or non-aromatic ring which may contain one sulfur, oxygen or nitrogen atom can be obtained as set forth in Scheme 1. In Scheme 1 a compound of formula (1) is first converted into its lithium or magnesium salt, transmetallated to the zinc derivative and then, in a transition metal (preferably palladium) catalyzed reaction, coupled with a compound of formula (2) to yield a compound of formula (3). The carboxylic acid ester group in the compound of formula (3) can be reduced , e.g. by means of a metal hydride such as diisobutyl-aluminum hydride to form a compound of formula (4) the hydroxymethyl group of which can be converted, e.g., by treatment with an oxidizing agent such as manganese dioxide, to yield a compound of formula II wherein A is formyl; $R^1$ is lower alkyl and $R^2$ is hydrogen;or $R^1$ and $R^2$ taken together with the carbon atoms to which they are attached form a 5–8 membered aromatic or non-aromatic ring which may contain one sulfur, oxygen or nitrogen atom.

Compounds of formula II wherein $R^1$ is lower alkyl and $R^2$ is halogen can be prepared as set forth in Scheme 2. According to Scheme 2, a compound of formula (5) is submitted to a Wittig-Horner reaction with a tri(lower alkyl) phosponoacetate to yield a compound of formula (6). The ester group in the compound of formula (6) is then converted into a formyl group by a two-step reduction and oxidation processs as described above to yield the compounds of formula (7) and (8), respectively. The compound of formula (8) can be halogenated by a halogenation-dehydrohalogenation procedure, e.g. by treatment with elementary halogen such as $Br_2$ followed by dehydrohalogenation with a strong base such as 1,8-diazabicyclo [5.4.0]undec-7-ene (DBU) to yield a compound of formula II wherein A is formyl, $R^1$ is lower alkyl and $R^2$ is halogen.

Compounds of formula II wherein the dotted bond is absent and $R^1$ and $R^2$ taken together are methylene can be obtained as set forth in Scheme 3. In Scheme 3 a compound of formula (1) is treated in a palladium catalyzed reaction with propargyl alcohol, to yield the acetylene compound (9). The hydroxy group in the propargyl alcohol can optionally be protected, e.g., by a trimethylsilyl group. Reduction of the triple bond in compound (9) affords compound (10) which is converted into compound (11) by a Simmons-Smith reaction. Compound (11) can be oxidized using methods known in the art, e.g., by pyridinium chlorochromate, or by a Swern- or Dess-Martin oxidation to yield a compound of formula II wherein A is formyl, the dotted bond is absent and $R^1$ and $R^2$ taken together are methylene.

Compounds of formula II wherein A is a triarylphosphonium or di(lower alkoxy)phosphinyl group can be prepared from compounds of formula II wherein A is formyl, by reducing the formyl group to a hydroxymethyl group in a manner known per se, e.g., by means of a complex metal hydride such as $NaBH_4$, replacing the hydroxy group by a bromine or chlorine atom, e.g., by treatment with a brominating or chlorinating agent such as phosphorous oxychloride or phosphorous tribromide and reacting the so-obtained bromide or chloride with a triarylphosphine or tri-(lower alkyl)phosphite. All these reactions can be carried out in a manner known per se.

The compounds of formula I and their salts can be used in the form of pharmaceutical preparations.

The preparations for systemic use can be produced e.g. by adding a compound of formula I or a salt thereof as the active ingredient to non-toxic, inert solid or liquid carriers which are usual in such preparations.

The preparations can be administered enterally, parenterally or topically. Preparations in the form of tablets, capsules, dragées, syrups, suspensions, solutions and suppositories are e.g. suitable for enteral administration.

Preparations in the form of infusion or injection solutions are suitable for parenteral administration.

For enteral and parenteral administration the compounds of formula I can be administered to adults in amounts of about 1–100 mg, preferably 5–30 mg/day.

For topical use the active substances are conveniently used in the form of salves, tinctures, creams, ointments, solutions, lotions, sprays, suspensions and the like. Salves and creams as well as solutions are preferred. These preparations designed for topical use can be produced by mixing the active ingredients with non-toxic, inert solid or liquid carriers which are suitable for topical treatment and which are usual in such preparations.

For topical use there are conveniently suitable about 0.1–5%, preferably 0.3–2%, solutions as well as about 0.1–5%, preferably 0.3–2%, salves or creams.

If desired, an antioxidant, e.g. tocopherol, N-methyl-γ-tocopheramine as well as butylated hydroxyanisole or butylated hydroxytoluene, can be admixed with the preparations.

The invention is illustrated further by the Examples which follow.

EXAMPLE 1

(2E,4E)-3-Methyl-5-[2-(5,5,8,8-tetramethyl-5,6,7,8-tetrahydro-naphthalen-2-yl)-phenyl]-penta-2,4-dienoic acid A. 5.4 g of 6-bromo-1,1,4,4-tetramethyltetralin were dissolved in 40 ml of tetrahydrofuran (THF) and 29 ml of a 1.5 m solution of tertiary butyllithium in pentane were added dropwise at −78° C. After 30 minutes a solution of 2.7 g of anhydrous zinc chloride in 80 ml of THF was added. After 30 minutes of stirring at −78° C. this solution was added slowly to a second reaction mixture kept at 0° C. and prepared in the following way: 0.7 g of bis (triphenylphosphine)palladium(II)-chloride were suspended in 60 ml of THF and 1.8 ml of a 20% solution of diisobutylaluminum hydride in toluene were added. After 15 minutes the black reaction mixture was cooled to 0° C. and a solution of 5 g of ethyl 2-iodo-benzoate in 70 ml of THF was added dropwise. After 15 minutes of stirring at 0° C. the first solution was added. The reaction mixture was stirred overnight at room temperature, poured at icewater, acidified with 2N hydrochloric acid and extracted several times with ethyl acetate. The combined organic phases were washed with water, dried over sodium sulfate and evaporated. The oily residue was chromatographed (silica gel, hexane/ethyl acetate=19:1) to give after recrystallization from hexane 2.6 g of 2-(5,5,8,8-tetramethyl-5,6,7,8-tetrahydro-naphthalen-2-yl)-benzoic acid ethyl ester as white crystals, m.p. 79°–81° C.

B. This material (2.6 g) was dissolved in 70 ml of THF and 32 ml of a 20% solution of diisobutylaluminum hydride in toluene was added dropwise at 0° C. After 2 hours of stirring at 0° C. 50 ml of a 1:1 mixture of methanol and water were added dropwise followed by addition of 25 ml of 6N hydrochloric acid. The reaction mixture was extracted with ethyl acetate, washed with water, dried and evaporated to give 2.4 g of a colourless oil which crystallized in the cold. Recrystallization from hexane gave 2-(5,5,8,8-tetramethyl-5,6,7,8-tetrahydro-naphthalen-2-yl)-benzylic alcohol, m.p. 111°–113° C.

C This alcohol (2.1 g) was dissolved in 50 ml of methylene chloride and 8.5 g of manganese dioxide were added. The reaction mixture was stirred overnight at room temperature, then filtered and evaporated to give 2.6 g of a colourless oil which was crystalllized from hexane and yielded 2.0 g of 2-(5,5,8,8-tetramethyl-5,6,7,8-tetrahydro-naphthalen-2-yl)-benzaldehyde, m.p. 85°–87° C.

D. 0.7 g of sodium hydride dispersion (50% in mineral oil) were washed 3 times with pentane, dried and suspended in 30 ml of THF. A solution of 3.0 g of 4-(diethoxyphosphinyl)-3-methyl-crotonic acid ethylester in 30 ml of THF was added slowly at 0° C. The reaction mixture was stirred for 1 hour at room temperature, cooled again to 0° C. and a solution of 2.2 g of the above mentioned aldehyde in 15 ml of THF was added dropwise. The reaction mixture was stirred at room temperature for about 3 hours, then poured on ice-water and extracted with ether. The organic phases were washed with water, dried and evaporated to give 5.9 g of a yellow oil which was purified by filtration through a silica gel column (solvent hexane/ethyl acetate=19:1) to afford 2.9 g of a colourless oil.

E. The oil (2.0 g) was dissolved in 50 ml of ethanol and a solution of 4.1 g of potassium hydroxide in 20 ml of water was added. After addition of 20 ml of THF, the solution was warmed to 40° C. for 4 hours. The cold reaction mixture was poured on icewater, acidified with 2N hydrochloric acid and extracted with ethyl acetate. The organic phases were washed with water, dried and evaporated to give a crystalline material. Recrystallization from a mixture of ethyl acetate and hexane yielded 1.6 g of (2E,4E)-3-methyl-5-[2-(5,5,8, 8-tetramethyl-5,6,7,8-tetrahydro-naphthalen-2-yl)-phenyl]-penta-2,4-dienoic acid as white crystals, m.p. 180°–182° C.

EXAMPLE 2

(2E,4E)-3-Methyl-5-[3-(5,5,8,8-tetramethyl-5,6,7,8-tetrahydro-naphthalen-2-yl)-thiophen-2-yl]-penta-2,4-dienoic acid In analogy to Example 1, this compound was synthesized starting with 6-bromo-1,1,4,4-tetramethyltetralin and methyl 3-iodo-2-thiophenecarboxylate, m.p. 188°–189° C.

EXAMPLE 3

(2E,4E)-3-Methyl-5-[2-(5,5,8,8-tetramethyl-5,6,7,8-tetrahydro-naphthalen-2-yl)-thiophen-3-yl]-penta-2,4-dienoic acid In analogy to Example 1, this compound was synthesized starting with 6-bromo-1,1,4,4-tetramethyltetralin and methyl-2-iodo-3-thiophenecarboxylate, m.p. 195°–197° C.

EXAMPLE 4

(2E,4E)-3-Methyl-5-[3-(5,5,8,8-tetramethyl-5,6,7,8-tetrahydro-naphthalen-2-yl)-thiophen-4-yl]-penta-2,4-dienoic acid In analogy to Example 1, this compound was synthesized starting with 6-bromo-1,1,4,4-tetramethyltetralin and methyl-3-iodo-4-thiophenecarboxylate, m.p. 192°–193° C.

EXAMPLE 5 a) 7.30 ml of phosphonoacetic acid triethyl ester were dissolved in 100 ml of abs. THF. 3.90 g of KOtBu were added at 0° C. and the mixture stirred for 15 minutes at this temperature. 4.20 g of 1-(5,5,8,8-tetramethyl-5,6,7,8-tetrahydro-naphthalen-2-yl)-ethanone, dissolved in 30 ml of THF, were added dropwise within 30 minutes at room temperature and stirring continued at 40° C. for 16 hours. The reaction mixture was then poured onto crashed ice/ $NH_4Cl$, extracted with EtOEt, washed with brine and $H_2O$, and dried over $Na_2SO_4$. Evaporation of the solvent, followed by flash chromatography (silica gel, hexane/AcOEt=97:3) yielded 3.70 g of (E)-3-(5,5,8,8-tetramethyl-5,6,7,8-tetrahydro-naphthalen-2-yl)-but-2-enoic acid ethyl ester as yellowish oil (GC-purity 98%).

b) 3.70 g of (E)-3-(5,5,8,8-tetramethyl-5,6,7,8-tetrahydro-naphthalen-2-yl)-but-2-enoic acid ethyl ester were dissolved in 38 ml of abs. THF. After cooling to −75° C. 26.7 ml of 1.2M DIBAL-H (toluene) were added by syringe within 5 minutes. After 10 minutes the reaction mixture was warmed to 0° C. and kept at this temperature for ½ hour. Since TLC indicated that some starting material was left, additional 3.0 ml of DIBAL-H were added at 0° C. After 15 minutes the reaction mixture was quenched with crashed ice/HCl and extracted with EtOEt. The organic extract was washed with $NaHCO_3$-solution and brine, dried over $Na_2SO_4$, and the solvents evaporated i.V. The remaining (E)-3-(5,5,8,8-tetramethyl-5,6,7,8-tetrahydro-naphthalen-2-yl)-but-2-en-1-ol (3.42 g) was used without further purification for the next step.

c) 3.42 g (E)-3-(5,5,8,8-tetramethyl-5,6,7,8-tetrahydro-naphthalen-2-yl)-but-2-en-1-ol were dissolved in 23 ml of $CH_2Cl_2$ and treated with 16.1 g of $MnO_2$. The reaction mixture was vigorously stirred at ambient temperature over night and then filtered through Celite. Evaporation of the solvent followed by flash chromatography (silica gel, hexane/AcOEt=92:8) afforded 2.86 g of (E)-3-(5,5,8,8-tetramethyl-5,6,7,8-tetrahydro-naphthalen-2-yl)-but-2-enal as pale yellow oil.

d) 2.86 g of (E)-3-(5,5,8,8-tetramethyl-5,6,7,8-tetrahydro-naphthalen-2-yl)-but-2-enal were dissolved in 16 ml of $CH_2Cl_2$ and cooled to −75° C. 1.1 eq. of $Br_2$ (0.63 ml), dissolved in 3 ml of $CH_2Cl_2$, was added drop by drop and the mixture kept for 10 minutes at this temperature. TLC indicated the formation of the dibromide. 4.98 ml of DBU was then added all at once and the temperature raised to 0° C. After ½ hour the reaction mixture was poured onto crushed ice/HCl, extracted with EtOEt, washed twice with brine, dried over $Na_2SO_4$ and the solvents removed i.V. Flash chromatography (silica gel, hexane/AcOEt=96:4) yielded 0.95 g of the labile (E)-2-bromo-3-(5,5,8,8-tetramethyl-5,6,7,8-tetrahydro-naphthalen-2-yl)-but-2-enal as yellow crystals of m.p. 115°–117° C. Double bond geometry was proven by NOE.

e) 290 mg of NaH (50% in mineral oil) was suspended in 8 ml of abs. THF and treated at 0° C. with 1.69 g of 4-(diethoxyphosphinyl)-3-methyl-crotonic acid ethyl ester. When the development of H2 had ceased (½ hour at 0° C.), 1.04 g of (E)-2-bromo-3-(5,5,8,8-tetramethyl-5,6,7,8-tetrahydro-naphthalen-2-yl)-but-2-enal, dissolved in 8 ml of abs. THF, was added and stirring continued for ¾ hour at 0° C. and for 1 hour at room temperature. The reaction mixture was then quenched with crashed ice and extracted with EtOEt. Twice washing with brine, drying over $Na_2SO_4$ and evaporation of the solvent afforded the crude product which was purified by flash chromatography (silica gel, hexane/AcOEt=98:2) to give 527 mg of (2E,4E,6E)-6-bromo-3-methyl-7-(5,5,8,8-tetramethyl-5,6,7,8-tetrahydro-naphthalen-2-yl)-octa-2,4,6-trienoic acid ethyl ester as yellow crystals of m.p. 97°–98.5° C.

f) 472 mg of (2E,4E,6E)-6-bromo-3-methyl-7-(5,5,8,8-tetramethyl-5,6,7,8-tetrahydro-naphthalen-2-yl)-octa-2,4,6-trienoic acid ethyl ester were dissolved in 10 ml of EtOH/THF=1:1 and treated with 2.65 ml of 2N aq. NaOH. The reaction mixture was stirred for 22 hours at ambient temperature in the dark. It was then poured onto crushed ice, extracted with AcOEt, washed with brine and $H_2O$, and dried over $Na_2SO_4$. Evaporation of the solvent and twofold crystallization (hexane/AcOEt=8:2) yielded finally 168 mg of (2E,4E,6E)-6-bromo-3-methyl-7-(5,5,8,8-tetramethyl-5,6,7,8-tetrahydro-naphthalen-2-yl)-octa-2,4,6-trienoic acid as yellow crystals of m.p. 189°–190° C.

EXAMPLE 6 a) 114 g of crude 2-bromo-(5,5,8,8-tetramethyl-5,6,7,8-tetrahydro-naphthalene (GC-purity: 76.5%) was dissolved in 250 ml of piperidine and successively treated with 4.80 g of $((Ph)_3P)_4Pd$, 0.95 g of CuI, and 1.35 g of $(Ph)_3P$. The internal temperature was then raised to 90°–95° C. and 150 ml of propargyloxy-trimethylsilane were added via dropping funnel within 4 hours. After 1 additional hour the reaction mixture was poured onto crashed ice/HCl conc. and vigorously stirred until TLC indicated that all silylether had been cleaved. EtOEt was added, the layers were separated and the organic phase washed with H$_2$O and brine. Drying over Na$_2$SO$_4$, evaporation of the solvent and purification by flash chromatography (silica gel, hexane/AcOEt=85:15) afforded 60.6 g of 3-(5,5,8,8-tetramethyl-5,6,7,8-tetrahydro-naphthalen-2-yl)-prop-2-yn-1-ol as ochre yellow crystals of m.p. 84°–85° C. (GC-purity >96%).

b) 30.3 g of 3-(5,5,8,8-tetramethyl-5,6,7,8-tetrahydro-naphthalen-2-yl)-prop-2-yn-1-ol were dissolved in 500 ml of abs. EtOH and hydrogenated at ambient temperature and 1 atm of H$_2$-pressure. The catalyst (Lindlar type A, 30 g) was added in three portions. The disappearance of starting material was followed by GC. After ca. 11 hours the catalyst was filtered off and the EtOH-solution evaporated to dryness to yield 30.9 g of (Z)-3-(5,5,8,8-tetrametbyl-5,6,7,8-tetrahydro-naphthalen-2-yl)-prop-2-en-1-ol as orange-coloured oil (GC-purity: 91.6%), which was used without further purification for the next step.

c) 12.5 g of Zn-dust (activated by washing with HCl, H$_2$O, EtOH, acetone, and EtOEt) and 1.89 g of freshly purified CuCl were refluxed in 120 ml of abs. EtOEt for 20 minutes. After cooling, 18.0 g of (Z)-3-(5,5,8,8-tetramethyl-5,6,7,8-tetrahydro-naphthalen-2-yl)-prop- 2-en-1-ol, dissolved in 40 ml of EtOEt, were added, followed by 15.2 ml of CH$_2$I$_2$. The mixture was kept under reflux for 16 hours. Afterwards, it was poured onto crashed ice, extracted with EtOEt, washed with H$_2$O, and dried over Na$_2$SO$_4$. Evaporation of the solvent and ensuing flash chromatography (silica gel, hexane/AcOEt=90:10) yielded 11.28 g of (1RS, 2SR)-2-(5,5,8,8-tetramethyl-5,6,7,8-tetrahydro-naphthalen-2-yl)-cyclopropylmethanol as yellowish oil (GC-purity: 97.6%).

d) 5.25 ml of freshly distilled oxalylchloride was dissolved in 130 ml of CH2Cl$_2$ and cooled to −62° C. 9.5 ml of abs. DMSO was slowly added (T raised to −52° C.). After 10 minutes, 14.35 g of (1RS,2SR)-2-(5,5,8,8-tetramethyl-5,6,7,8-tetrahydro-naphthalen-2-yl)-cyclopropylmethanol, dissolved in 30 ml of CH$_2$Cl$_2$, was added dropwise at −60° C. After 15 minutes, 38.7 ml of NEt$_3$ was added and the cooling bath was removed. 1 hour later, the reaction mixture was quenched with crashed ice, extracted with EtOEt, washed with brine and H$_2$O, dried over Na$_2$SO$_4$, and evaporated i.V. Flash chromatography (silica gel, hexane/AcOEt= 94:6) afforded 12.52 g of (1RS,2SR)-2-(5,5,8,8-tetramethyl-5,6,7,8-tetrahydro-naphthalen-2-yl)-cyclopropylcarbaldebyde as pale yellow oil.

e) 2.34 g of NaH (50% in mineral oil) was suspended in 120 ml of abs. DMF and treated at 0° C. with 16.8 g of 4-(diethoxyphosphinyl)-3-methyl-crotonic acid ethyl ester. When the development of H$_2$ had ceased (ca. ½ hour at 0° C.), 12.5 g of (1RS,2SR)-2-(5,5,8,8-tetramethyl-5,6,7,8-tetrahydro-naphthalen-2-yl)-cyclopropyl-carbaldehyde, dissolved in 25 ml of abs. DMF, was slowly added at 0° C. Stirring was continued for 30 minutes. The reaction mixture was then poured onto EtOH/H$_2$O=8:2 and extracted with hexane. The hexane-layer was dried over Na$_2$SO$_4$ and evaporated i.V. Flash chromatography (silica gel, hexane/ AcOEt=98.5:1.5) yielded 8.85 g of (2E,4E)-3-methyl-5-[(1RS,2RS)-2-(5,5,8,8-tetramethyl-5,6,7,8-tetrahydro-naphthalen-2-yl)-cyclopropyl]-penta-2,4-dienoic acid ethyl ester as colourless oil (ca. 94% pure according to $^1$H-NMR) besides 8.46 g of E/Z-mixture ((2E,4E)/(2Z,4E)=ca. 2:1).

f) 8.84 g of (2E,4E)-3-methyl-5-[(1RS,2RS)-2-(5,5,8,8-tetramethyl-5,6,7,8-tetrahydro-naphthalen-2-yl)-cyclopropyl]-penta-2,4-dienoic acid ethyl ester (ca. 94% pure according to $^1$H-NMR) was dissolved in 100 ml of THF/EtOH=1:1 and treated with 40 ml of 3N aq. NaOH. The reaction mixture was kept in the dark at ambient temperature for three days. It was then poured onto crashed ice, extracted with EtOEt, washed with H$_2$O, and dried over Na$_2$SO$_4$. Evaporation of the solvent and twofold crystallisation (hexane/AcOEt=8:2 and 7:3) yielded 4.25 g of (2E,4E)-3-methyl-5-[(1RS,2RS)-2-(5,5,8,8-tetramethyl-5,6,7,8-tetrahydro-naphthalen-2-yl)-cyclopropyl]-penta-2,4-dienoic acid as white crystals of m.p. 150°–151° C.

EXAMPLE 7

In analogy to Example 6 e) and f) there was prepared (2E,4E)-3-Methyl-5[(1S,2S)-2-(5,5,8,8-tetramethyl-5,6,7,8-tetrahydro-naphthalen-2-yl)-cyclopropyl]-penta-2,4-dienoic acid as white crystals of mp. 108°–110°, $a_D^{RT}$=+161° (CHCl$_3$, c=0.8%),from (1R,2S)-2-(5,5,8,8-tetramethyl-5,6,7,8-tetrahydro-naphthalen-2-yl)-cyclopropylcarbaldehyde and 4-(diethoxyphosphinyl)-3-methyl-crotonic acid ethyl ester by Wittig-Horner-reaction, separation of double bond isomers and base-catalyzed hydrolysis. The prerequisite aldehyde was synthesized, using as key step an enantioselective cyclopropanation as described in Chemistry Letters 1992, 61, and ensuing Swern—oxidation, as follows:

1.67 g of of (Z)-3-(5,5,8,8-tetramethyl-5,6,7,8-tetrahydro-naphthalen-2-yl)-prop-2-en-1-ol were dissolved in 36 ml of CH$_2$Cl$_2$. At 0° C. 7.62 ml of Et$_2$Zn-solution (1M[hexane]) was added, followed 15 min. later by 1.33 ml of L-(+)-diethyl tartrate, dissolved in 18 ml of CH$_2$Cl$_2$. Stirring was continued for 45 min. The reaction flask was then cooled to −22° C. and another portion of 13.8 ml of Et$_2$Zn-solution (1M[hexane]) was added, followed by 2.23 ml of CH$_2$I$_2$. The reaction flask was allowed to reach +18° C. during 16 h. After quenching with crushed ice/NH$_4$Cl-solution, the mixture was extracted with EtOEt, washed with dil. HCI and H$_2$O, dried over Na$_2$SO$_4$ and evaporated to dryness. Flash chromatography (silica gel, hexane/AcOEt=87/13) yielded 1.057 g of (1R,2S)-2-(5,5,8,8-tetramethyl-5,6,7,8-tetrahydro-naphthalen-2-yl)-cyclopropylmethanol, 99% pure according to GC. The absolute configuration was assigned in analogy to Chemistry Letters 1992, 61, but not rigorously proven; the optical purity was determined at the next stage.

381 ml of freshly distilled oxalylchloride was dissolved in 13 ml of CH$_2$Cl$_2$ and cooled to −65°. 687 ml of abs. DMSO, dissolved in 4 ml of CH$_2$Cl$_2$, was slowly added. After 10 min., 1.04 g of (1R,2S)-2-(5,5,8,8-tetramethyl-5,6,7,8-tetrahydro-naphthalen-2-yl)-cyclopropylmethanol, dissolved in 11 ml of CH$_2$Cl$_2$, was added dropwise at −65°. After 10 min., 2.79 ml of NEt$_3$ was added and the cooling bath was removed. 1 h later, the reaction mixture was quenched with crushed ice, extracted with EtOEt, washed with brine and H$_2$O, dried over Na$_2$SO$_4$, and evaporated i.V. Flash chromatography (silica gel, hexane/AcOEt=9/1) yielded 876 mg of (1R,2S)-2-(5,5,8,8-tetramethyl-5,6,7,8-tetrahydro-naphthalen-2-yl)-cyclopropylcarbaldehyde as pale yellow oil, 99% pure according to GC.

The optical purity was determined as follows (cf. J. Org. Chem. 46, 5159, 1981):

22mg of (1R,2S)-2-(5,5,8,8-tetramethyl-5,6,7,8-tetrahydro-naphthalen-2-yl)-cyclopropylcarbaldehyde were dissolved in 0.5 ml toluene and treated subsequently with 30 mg of MgSO$_4$.2H$_2$O, 1 mg of pTsOH, and 16 ml of D-(−)-2,3-butane-diol. The mixture was kept for 110 min. at 50°. Then it was poured onto crushed ice, extracted with EtOEt, washed with H$_2$O, dried over Na$_2$SO$_4$, and evaporated i.V. GC-analysis indicated a diastereomeric ratio of 91.9/3.90, corresponding to an e.e. of 92%. The $^1$H-NMR-spectrum was in full agreement with this analysis.

EXAMPLE 8

In analogy to Example 7, but using D-(−)-diethyl tartrate in the cyclopropanation step, there was prepared (2E,4E)-3-Methyl-5-[(1R,2R)-2-(5,5,8,8-tetramethyl-5,6,7,8-tetrahydro-naphthalen-2-yl)-cyclopropyl]-penta-2,4-dienoic acid as white crystals of mp. 93°–96°, $a_D{}^{RT}$=−156° (CHCl$_3$, c=0.9%),

EXAMPLE 9

(2E,4E)-3-Methyl-5-[2-(5,5,8,8-tetramethyl-5,6,7,8-tetrahydro-naphthalen-2-yl)-cyclopent-1-enyl]-penta-2,4-dienoic acid ethyl ester 1.59 g of 2-Bromo-5,5,8,8-tetramethyl-5,6,7,8-tetrahydro-naphthalene were dissolved in 12 ml of THF and treated at −75° with 4.37 ml of 1.5M nBuLi (hexane). After 15 min 850 mg of scrupulously dried ZnCl$_2$, dissolved in 9 ml of THF, were added and the mixture stirred at −75° for ½ h.

In the meantime, 210 mg of ((Ph)$_3$P)$_2$PdCl$_2$ were suspended in a second flask containing 12 ml of THF and reduced by adding via syringe 497 ml of DIBAL-H (1.2M [toluene]). After stirring for 1 h at 0°, 1.70 g of (2E,4E)-5-(2-bromo-cyclopent-1-enyl)-3-methyl-penta-2,4-dienoic acid ethyl ester, dissolved in 6 ml of THF, was added to the resultant black Pd°-solution, followed by the above prepared arylzinc-solution which was transferred via a double-ended needle The whole mixture was kept at ambient temperature for 1 h, then poured onto crushed ice and extracted with EtOEt. Washing with sat. NaCl-solution, drying over Na$_2$SO$_4$, and evaporation to dryness left a crude product which was purified by flash chromatography (silica gel, hexane/AcOEt=96/4) and finally crystallized from hexane to give 1.372 g of the title compound as yellowish crystals of mp. 83°–86°.

The prerequisite (2E,4E)-5-(2-bromo-cyclopent-1-enyl)-3-methyl-penta-2,4-dienoic acid ethyl ester was synthesized as follows:

2.03 g of NaH (50% in mineral oil) was suspended in 120 ml of DMF. 12.9 g of 4-(diethoxy-phosphinyl)-3-methyl-but-2-enoic acid ethyl ester was added at 0°. The mixture was stirred for 15 min at 0° and for 30 min at RT. After recooling to 0°, 5.72 g of 2-bromo-cyclopent-1-enecarbaldehyde, dissolved in 11 ml of DMF, was added drop by drop and allowed to react for 10 min. at 0° and for 2 h at RT. The mixture was then poured onto crushed ice, extracted with EtOEt, washed with sat. NaCi-solution, dried over Na$_2$SO$_4$, and evaporated to dryness. Purification of the residue by flash chromatography (silica gel, hexane/AcOEt=97/3) and crystallization from hexane/trace amounts of AcOEt yielded finally 3.408 g of pure (2E,4E)-5-(2-bromo-cyclopent-1-enyl)-3-methyl-penta-2,4-dienoic acid ethyl ester as yellowish crystals of mp. 85°–86°.

EXAMPLE 10

(2E,4E)-3-Methyl-5-[2-(5,5,8,8-tetramethyl-5,6,7,8-tetrahydro-naphthalen-2-yl)-cyclopent-1-enyl]-penta-2,4-dienoic acid 1.32 g of (2E,4E)-3-Methyl-5-[2-(5,5,8,8-tetramethyl-5,6,7,8-tetrahydro-naphthalen-2-yl)-cyclopent-1-enyl]-penta-2,4-dienoic acid ethyl ester was dissolved in 13 ml of THF/EtOH=1/1 and treated with 5.6 ml of 3N NaOH. The mixture was kept for 48 h at ambient temperature and then poured onto crushed ice/HCl. Extraction with AcOEt, washing with H$_2$O, drying over Na$_2$SO$_4$, evaporation of the solvent, and recrystallization from AcOEt afforded 803 mg of the title compound as yellow crystals of mp. 195°–196° (dec.).

EXAMPLE 11

In analogy to example 10 there were prepared:
(2E,4E)-3-Methyl-5-[2-(5,5,8,8-tetramethyl-5,6,7,8-tetrahydro-naphthalen-2-yl)-cyclohept-1-enyl]-penta-2,4-dienoic acid as yellow crystals of mp. 159°–160°; and
(2E,4E)-3-Methyl-5-[2-(5,5,8,8-tetramethyl-5,6,7,8-tetrahydro-naphthalen-2-yl)-cyclohex-1-enyl]-penta-2,4-dienoic acid as yellowish crystals of mp. 202°–203°.

EXAMPLE A

Hard gelatine capsules can be produced as follows:

| Ingredients | mg/capsule |
|---|---|
| 1. Spray-dried powder containing 75% of compound I | 20 |
| 2. Sodium dioctylsulphosuccinate | 0.2 |
| 3. Sodium carboxymethylcellulose | 4.8 |
| 4. Microcrystalline cellulose | 86.0 |
| 5. Talc | 8.0 |
| 6. Magnesium stearate | 1.0 |
| Total | 120 |

The spray-dried powder, which is based on the active ingredient, gelatine and microcrystalline cellulose and which has an average particle size of the active ingredient of <1 m (measured by means of autocorrelation spectroscopy), is moistened with an aqueous solution of sodium carboxymethylcellulose and sodium dioctyl-sulphosuccinate and kneaded. The resulting mass is granulated, dried and sieved, and the granulate obtained is mixed with microcrystalline cellulose, talc and magnesium stearate. The powder is filled into size 0 capsules.

EXAMPLE B

Tablets can be produced as follows:

| Ingredients | mg/tablet |
|---|---|
| 1. Compound I as a finely milled powder | 20 |
| 2. Pdwd. lactose | 100 |
| 3. White corn starch | 60 |
| 4. Povidone K30 | 8 |
| 5. White corn starch | 112 |
| 6. Talc | 16 |
| 7. Magnesium stearate | 4 |
| Total | 320 |

The finely milled active ingredient is mixed with lactose and a portion of the corn starch. The mixture is moistened with an aqueous solution of Povidone K30 and kneaded, and the resulting mass is granulated, dried and sieved. The granulate is mixed with the remaining corn starch, talc and magnesium stearate and pressed to tablets of suitable size.

EXAMPLE C

Soft gelatine capsules can be prepared as follows:

| Ingredients | mg/capsule |
| --- | --- |
| 1. Compound I | 5 |
| 2. Triglyceride | 450 |
| Total | 455 |

10 g of compound I are dissolved in 90 g of medium-chain triglyceride while stirring and under inert gasification and protection from light. The solution is processed as a capsule fill mass to soft gelatine capsules containing 5 mg of active ingredient.

EXAMPLE D

A lotion can be produced as follows:

| Ingredients | |
| --- | --- |
| 1. Compound I finely milled | 1.0 g |
| 2. Carbopol 934 | 0.6 g |
| 3. Sodium hydroxide | q.s. ad pH 6 |
| 4. Ethanol, 94% | 50.0 g |
| 5. Demineralized water | ad 100.0 g |

The active ingredient is incorporated into the 94% ethanol/water mixture with protection from light. Carbopol 934 is stirred in until gelling is complete and the pH value is adjusted with sodium hydroxide.

We claim:
1. Compounds of the formula I

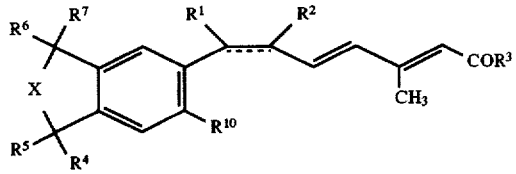

wherein the dotted bond is optional; and, when the dotted bond is present, $R^1$ is lower alkyl and $R^2$ is halogen, or $R^1$ and $R^2$ taken together with the carbon atoms to which they are attached form a 5–8 membered carbocyclic ring or a 5–8 membered heterocyclic ring containing one sulfur, oxygen or nitrogen atom, wherein, when said ring is aromatic, the dotted bond is part of the mesomeric system; or, when the dotted bond is absent, $R^1$ and $R^2$ taken together are methylene to form a cis-substituted cyclopropyl ring; $R^3$ is hydroxy or lower alkoxy; $R^4$, $R^5$, $R^6$ and $R^7$ are, independently, hydrogen or lower alkyl; X is $(>CR^8R^9)_n$; and n is 1,2 or 3; $R^8$, $R^9$ are, independently, hydrogen or lower alkyl; $R^{10}$ is hydrogen, alkyl or alkoxy; and pharmaceutically acceptable salts of carboxylic acids of formula I.

2. Compounds as in claim 1 of the formula

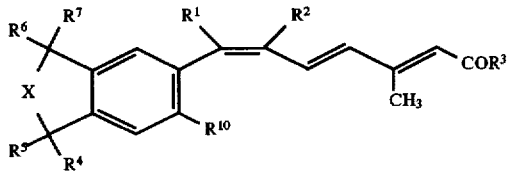

wherein $R^1$ is lower alkyl and $R^2$ is halogen, or $R^1$ and $R^2$ taken together with the carbon atoms to which they are attached form a 5–8 membered carbocyclic ring or a 5–8 membered heterocyclic ring containing one sulfur, oxygen or nitrogen atom, wherein, when said ring is aromatic, the double bond between the carbon atoms adjacent to $R^1$ and $R^2$ is part of the mesomeric system; $R^3$–$R^7$, $R^{10}$ and X are as in formula I;

and pharmaceutically acceptable salts of carboxylic acids of formula Ia.

3. A compound of formula Ia

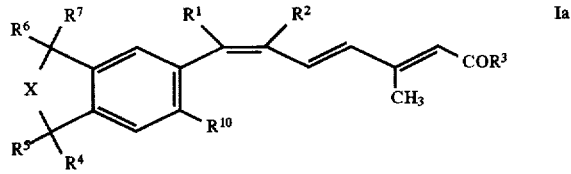

wherein $R_1$ and $R_2$ taken together with the carbon atoms to which they are attached form a 5–8 membered carbocyclic ring; $R_3$ is hydroxy or lower alkoxy; $R_4$, $R_5$, $R_6$, and $R_7$ are, independently, hydrogen or lower alkyl; X is $(>CR_8R_9)_n$; and n is 1,2, or 3; $R_8$ and $R_9$ are, independently, hydrogen or lower alkyl; $R_{10}$ is hydrogen, alkyl or alkoxy; and pharmaceutically acceptable salts of carboxylic acids of formula Ia.

4. A compound which is (2E,4E)-3-methyl-5-[2-(5,5,8,8-tetramethyl-5,6,7,8-tetrahydro-naphthalen-2-yl)-cyclopent-1-enyl]-penta-2,4-dienoic acid ethyl ester.

5. A compound which is (2E,4E)-3-methyl-5-[2-(5,5,8,8-tetramethyl-5,6,7,8-tetrahydro-naphthalen-2-yl)-cyclopent-1-enyl]-penta-2,4-dienoic acid.

6. A compound which is (2E,4E)-3-methyl-5-[2-(5,5,8,8-tetramethyl-5,6,7,8-tetrahydro-naphthalen-2-yl)-cyclohept-1-enyl]-penta-2,4-dienoic acid.

7. A compound which is (2E,4E)-3-methyl-5-[2-(5,5,8,8-tetramethyl-5,6,7,8-tetrahydro-naphthalen-2-yl)-cyclohex-1-enyl]-penta-2,4-dienoic acid.

8. Compounds as in claim 2 wherein $R^1$ and $R^2$ taken together with the carbon atoms to which they are attached form a phenylene ring.

9. A compound which is (2E,4E)-3-methyl-5-[2-(5,5,8,8-tetramethyl-5,6,7,8-tetrahydro-naphthalen-2-yl)-phenyl]-penta-2,4-dienoic acid.

10. A compound of formula Ia

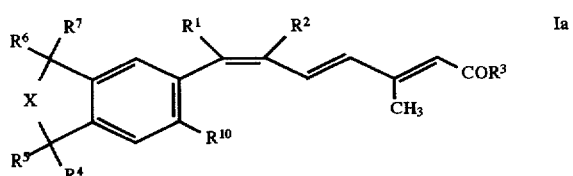

wherein $R_1$ and $R_2$ taken together with the carbon atoms to which they are attached form a 5–8 membered heterocyclic ring containing one sulfur, oxygen, or nitrogen atom and the double bond between the carbon atoms adjacent to $R_1$ and $R_2$ is part of the mesomeric system; $R_3$ is hydroxy or lower alkoxy; $R_4$, $R_5$, $R_6$, and $R_7$ are, independently, hydrogen or lower alkyl; X is $(>CR_8R_9)_n$; and n is 1,2, or 3; $R_8$ and $R_9$ are, independently, hydrogen or lower alkyl; $R_{10}$ is hydrogen, alkyl or alkoxy; and pharmaceutically acceptable salts of carboxylic acids of formula Ia.

11. A compound as in claim 10 which is (2E,4E)-3-methyl-5-[3-(5,5,8,8-tetramethyl-5,6,7,8-tetrahydro-naphthalen-2-yl)-thiophen-2-yl]-penta-2,4-dienoic acid.

12. A compound as in claim 10 which is (2E,4E)-3-methyl-5-[2-(5,5,8,8-tetramethyl-5,6,7,8-tetrahydro-naphthalen-2-yl)-thiophen-3-yl]-penta-2,4-dienoic acid.

13. A compound as in claim 10 which is (2E,4E)-3-methyl-5-[3-(5,5,8,8-tetramethyl-5,6,7,8-tetrahydro-naphthalen-2-yl)-thiophen-4-yl]-penta-2,4-dienoic acid.

14. Compounds as in claim 2 wherein $R^2$ is halogen.

15. A compound which is (2E,4E,6E)-6-bromo-3-methyl-7-(5,5,8,8-tetramethyl-5,6,7,8-tetrahydro-naphthalen-2-yl)-octa-2,4,6-trienoic acid ethyl ester.

16. A compound which is (2E,4E,6E)-6-bromo-3-methyl-7-(5,5,8,8-tetramethyl-5,6,7,8-tetrahydro-naphthalen-2-yl)-octa-2,4,6-trienoic acid.

17. Compounds of the formula

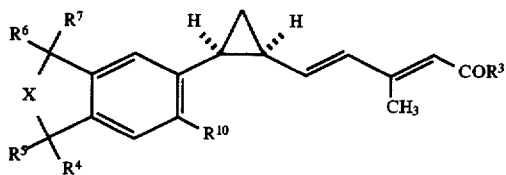

Ib wherein $R^3$–$R^7$, $R^{10}$ and X are as in formula I;
and pharmaceutically acceptable salts of carboxylic acids of formula Ib.

18. A compound as in claim 17, which is (2E,4E)-3-methyl-5-[(1RS,2RS)-2-(5,5,8,8-tetramethyl-5,6,7,8-tetrahydro-naphthalen-2-yl)-cyclopropyl]-penta-2,4-dienoic acid.

19. A compound as in claim 17, which is (2E,4E)-3-methyl-5-[(1S,2S)-2-(5,5,8,8-tetramethyl-5,6,7,8-tetrahydro-naphthalen-2-yl)-cyclopropyl]-penta-2,4-dienoic acid.

20. A compound as in claim 17, which is (2E,4E)-3-methyl-5-[(1R,2R)-2-(5,5,8,8-tetramethyl-5,6,7,8-tetrahydro-naphthalen-2-yl)-cyclopropyl]-penta-2,4-dienoic acid.

21. Compounds of formula II

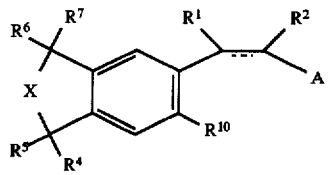

II wherein A is formyl, or di-(lower alkoxy)phosphinyl; and $R^1$, $R^2$, $R^4$, $R^5$, $R^6$, $R^7$ and $R^{10}$ are as defined in claim 1.

22. A pharmaceutical composition comprising a compound of formula I of claim 1 or pharmaceutically acceptable salt thereof, and a pharmaceutically acceptable carrier.

* * * * *